(12) United States Patent
Dominguez

(10) Patent No.: US 7,456,325 B2
(45) Date of Patent: Nov. 25, 2008

(54) PROCESS FOR THE PRODUCTION OF A HYDROXYALKYNE BY COUPLING REACTION BETWEEN ACETALDEHYDE AND A TERMINAL ALKYNE

(75) Inventor: Beatriz Dominguez, Suffolk (GB)

(73) Assignee: Johnson Matthey PLC, London (GB)

( * ) Notice: Subject to any disclaimer, the term of this patent is extended or adjusted under 35 U.S.C. 154(b) by 355 days.

(21) Appl. No.: 10/553,464

(22) PCT Filed: Apr. 15, 2004

(86) PCT No.: PCT/GB2004/001639

§ 371 (c)(1),
(2), (4) Date: Oct. 17, 2005

(87) PCT Pub. No.: WO2004/092098

PCT Pub. Date: Oct. 28, 2004

(65) Prior Publication Data

US 2007/0004943 A1    Jan. 4, 2007

(30) Foreign Application Priority Data

Apr. 15, 2003    (GB)    ................... 0308672.5

(51) Int. Cl.
*C07C 33/044*    (2006.01)
*C07C 33/046*    (2006.01)
(52) U.S. Cl. .................................... 568/855
(58) Field of Classification Search ................ 568/855
See application file for complete search history.

(56) References Cited

U.S. PATENT DOCUMENTS 5,110,996 A    5/1992    Evans et al.

FOREIGN PATENT DOCUMENTS

WO    WO-02/094741 A1    11/2002

OTHER PUBLICATIONS

Kuo-Ming Wu et al., "Structural Effects on [1,5]-Sigmatropic Hydrogen Shifts of Vinylallenes," *J. Org. Chem.*, vol. 55, No. 14, 1990, pp. 4381-4392.
Jordi Bach et al, "Stereoselective Reduction of Unsaturated 1,4 Diketones. A Practical Route to Chiral 1,4-Diols," *Tetrahedron Letters*, vol. 38, No. 6, 1997, pp. 1091-1094.
Mark J. Burk et al., "Highly Enantioselective Hydrogenation of β-Keto Esters under Mild Conditions," *J. Amer. Cehm. Soc.*, vol. 117, No. 15, 1995, pp. 4423 and 4424.
D. Boyall et al., "Enantioselective Addition of 2-Methyl-3-butyn-2-ol to Aldehydes: Preparation of 3-Hydroxy-1-butynes," *Organic Letters*, Vo. 2, No. 26, 2000, pp. 4233-4236.
Doug E. Frantz et al., "Facile Enantioselective Synthesis of Propargylic Alcohols by Direct Addition of Terminal Alkynes," *J. Am. Chem. Soc.*, 2000, vol. 122, pp. 1806-1807.
Abstract No. XP-00289664, Beilstein Institute for Organic Chemistry, © 1988-2001.
Abstract No. XP-002289665, Beilstein Institute for Organic Chemistry, © 1988-2001.
Abstract No. XP-002289666, Beilstein Institute for Organic Chemistry, © 1988-2001.
Abstract No. XP-002289667, Beilstein Institute for Organic Chemistry, © 1988-2001.

*Primary Examiner*—Elvis O. Price
(74) *Attorney, Agent, or Firm*—RatnerPrestia

(57) ABSTRACT

A process for performing, a coupling reaction between acetaldehyde and a terminal alkyne to yield a hydroxyalkyne is described comprising the steps of; (i) reacting without solvent, a terminal alkyne with a Lewis acidic metal salt in the presence of a alkanolamine ligand and a cyclic amine base to form a metal-alkyne complex, and (ii) adding a solution of acetaldehyde to the metal-alkyne complex.

7 Claims, No Drawings

PROCESS FOR THE PRODUCTION OF A HYDROXYALKYNE BY COUPLING REACTION BETWEEN ACETALDEHYDE AND A TERMINAL ALKYNE

This application is the U.S. national phase application of PCT International Application No. PCT/GB2004/001639, filed Apr. 15, 2004, and claims priority of British Patent Application No. 0308672.5, filed Apr. 15, 2003.

FIELD OF THE INVENTION

This invention relates to a process for performing a coupling reaction between acetaldehyde and alkynes to produce hydroxyalkynes and their derivatives.

The asymmetric coupling reaction of aldehydes and alkynes to produce hydroxyalkynes and their derivatives is of interest to the fine chemicals industry where it provides a source of asymmetry useful in preparing chiral products such as pharmaceutical intermediates.

BACKGROUND OF THE INVENTION

The asymmetric coupling reaction of aldehydes and alkynes is known. In particular, the preparation of chiral propargyl alcohols, such as 3-hydroxy-1-butyne, using zinc triflate in an enantioselective aldehyde addition reaction with a terminal alkyne, in the presence of triethylamine and (+)- or (−)-N-methylephedrine has been described. (See for example, Carreira et al, *Organic Letters,* 2000, 2(26), 4233-4236 and Carreira et al, *J. Am. Chem. Soc.,* 2000, 122, 1806-1807). By the term 'terminal' we mean an alkyne having a hydrogen atom bound to one carbon atom forming the carbon-carbon triple bond, i.e. a C≡C—H group. This reaction has been used to provide chiral propargyl alcohols, via, for example, thermally unstable alkynediols. However these workers have only considered aldehydes having 3 or more carbon atoms. Similarly, WO 02/094741 describes a process for performing coupling reactions to prepare 1,4-, 1,5- or 1,6-diols from aldehydes and hydroxyalkynes wherein the aldehydes are of general formula $R^1C(O)H$ in which $R^1$ represents a saturated or unsaturated alkyl having between 2 and 24 carbon atoms, cycloalkyl or aryl group.

Acetaldehyde ($CH_3CHO$) has presented practical challenges that have prevented its successful use in Lewis acid mediated coupling reactions such as those described above. In particular, the propensity of acetaldehyde for self-condensation to form mixed oligomeric species has presented a significant obstacle. Consequently, useful acetaldehyde-derived products such as chiral alkynes and chiral 1,4-diols and their derivatives have not been successfully obtained in commercially attractive yields.

SUMMARY OF THE INVENTION

In the present invention the coupling reaction of acetaldehyde and terminal alkynes may be performed in high yield.

Accordingly this invention provides a process for performing a coupling reaction between acetaldehyde and a terminal alkyne to yield a hydroxyalkyne comprising the steps of;

i) reacting without solvent, a terminal alkyne with a Lewis acidic metal salt in the presence of an alkanolamine ligand and a cyclic amine base to form a metal-alkyne complex, and ii) adding a solution of acetaldehyde to the metal-alkyne complex.

DETAILED DESCRIPTION OF THE INVENTION

Acetaldehyde as commercially provided may contain small amounts of water and/or oligomeric species formed by self-condensation reactions. While such crude acetaldehyde may be used in the process of the present invention, it is preferable to purify the acetaldehyde before use, e.g. by distillation or drying using suitable molecular sieves.

The terminal alkyne used for preparing the hydroxyalkyne may be any alkyne having a terminal hydrogen, i.e. a C≡C—H group, for example liquid acetylene in a pressurised, sealed vessel may be used. However, a particularly useful group of terminal alkynes are those liquid alkynes that may undergo thermal fragmentation reactions. These alkynes are readily available and relatively easy to handle compared to acetylene. Thus in one embodiment, the terminal alkyne is of general formula $R^1R^2C(OH)C≡CH$ in which $R^1$ and $R^2$ may be the same or different and are selected from the group comprising methyl, ethyl and propyl. Preferably $R^1$ and $R^2$ are methyl and a preferred alkyne is 2-methyl-3-butyn-2-ol. In a second embodiment, the alkyne is an alkyne-silane, for example (trimethylsilyl)acetylene. Such suitable alkynes are depicted below.

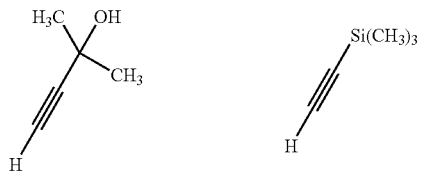

Step (i) of the process of the present invention requires reaction of the alkyne with a Lewis acidic metal salt to form a metal-alkyne complex. The Lewis acidic metal is preferably zinc, iridium(I) or indium and the salt is preferably a metal triflate (i.e. a metal trifluoromethanesulphonate). Most preferably the Lewis acidic metal salt is zinc triflate. The Lewis acid may if desired be supported on an insoluble support material, for example a polymeric support or an inorganic support such as silica, a metal oxide, zeolite or an aluminosilicate to facilitate catalyst recovery and re-use.

A cyclic amine base is present during the first step of the process of the present invention. By 'cyclic amine base' we mean a basic amine wherein at least one nitrogen atom forms part of a ring structure. In particular we have found that the tertiary alkyl amine catalysts used heretofore such as triethylamine when used in the process of the present invention do not provide the desired hydroxyalkyne products reproducibly or in high yield. Preferably the cyclic amine base is selected from the group comprising 1,8-diazabicyclo[5.4.0]undec-7-ene (DBU), 1,5-diazabicyclo-[4.3.0]non-5-ene (DBN) and 1,4-diazabicyclo[2.2.2]octane (DBN), particularly DBU.

The process further requires the presence, during step (i), of an alkanolamine ligand. Preferably the alkanolamine is a tertiary alkanolamine (i.e. $NR'_3$ where R'=alkyl or cycloalkyl) and the hydroxyl group is in a β-position to the nitrogen atom. Also, preferably either a chiral (+) or (−) alkanolamine ligand is used that interacts with the metal-alkyne complex to direct the chirality of the hydroxyalkyne reaction product. The terms "(+)" or "(−)" here refer to the effect of the molecular structure on the direction of rotation of plane polarized light. Hence, for example a single enantiomer (+)-ligand may provide a reaction product with a greater number of (R)-chiral centres and a (−)-ligand likewise may provide a product with a greater number of (S)-chiral centres. Hence, the alkanolamine ligand is most preferably a chiral β-alkanolamine having a tertiary amine group. Suitable alkanolamine ligands are depicted below.

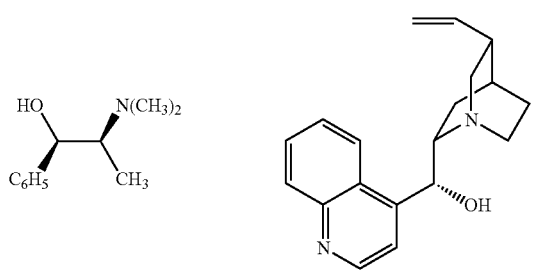

Most preferably the alkanolamine ligand is (+)- or (−)-N-alkyl- or aryl-ephedrine, especially (+)- or (−)-N-methyl-ephedrine. In the process of the present invention (+)-N-methylephedrine produces predominantly (R)-chiral centres whilst (−)-N-methylephedrine produces predominantly (S)-chiral centres.

The product of process of the present invention is a hydroxyalkyne having a hydroxymethyl group bound to the alkyne [e.g. $R^1R^2C(OH)C\equiv CCH(OH)CH_3$]. Preferably the product is a chiral hydroxyalkyne, the chiral centre being the carbon atom to which the hydroxyl and methyl groups derived from the acetaldehyde molecule are bound. Depending on whether the (+) or (−) alkanolamine ligand was used the product hydroxyalkyne may have predominantly an (R−) or (S−) configuration at the chiral centre. Furthermore, if the alkyne starting material was itself chiral and possessed predominantly an (R)- or (S)-chiral centre (opposed to a racemic mixture), the product hydroxyalkyne may be homochiral, i.e., (R,R) or (S,S) or have one (R) and one (S) centre. Herein the term "chiral" refers to a molecular structure that does not have an improper rotation axis ($S_n$), i.e., it belongs to point group $C_n$ or $D_n$. Such molecules are thus chiral with respect to an axis, plane or centre of asymmetry. The term "homochiral" refers to a structure having two, or more, chiral centres having the same conformation.

Step (i) of the process of the present invention is performed in the absence of an additional solvent. By 'absence of an additional solvent' we mean that the reaction is performed between the terminal alkyne, Lewis acidic metal salt, cyclic amine base and alkanolamine ligand substantially in the absence of a further solubilising substance. The reaction conditions employed should therefore be such that the alkyne is able to react with the Lewis acidic metal salt in the liquid phase. To facilitate mixing, the terminal alkyne is preferably used in excess. i.e. the alkyne in excess acts as the medium for its reaction with the Lewis acidic metal salt and the reaction mixture in step (i) therefore consists of terminal alkyne, Lewis acidic metal salt, cyclic amine base and alkanolamine ligand. Step (ii) of the process of the present invention requires that the acetaldehyde is diluted with a solvent. The acetaldehyde if preferably added slowly and/or in high dilution to reduce the amount of self-condensation. The solvent may be a hydrocarbon, an aromatic hydrocarbon, an ether, an alcohol or a chlorinated hydrocarbon. Examples of suitable solvents include dichloromethane, diethylether, tetrahydrofuran, ethanol, iso-propanol, heptanes, toluene and xylene. The preferred solvent for acetaldehyde is toluene. To avoid excessive amounts of solvent, the acetaldehyde concentration is preferably greater than 0.1 moles/liter. To avoid acetaldehyde self-condensation the maximum concentration is preferably less than 2 mole/liter, more preferably less than 1 mole/liter and most preferably less than 0.5 mole/liter.

Step (i) of the process of the present invention is preferably performed under mild conditions. For example, the reactions may be performed at temperatures ranging from −20 to 80° C. over a period of 0.5 to 24 hours. Preferably the reaction is performed at 15-60° C. over a period of 1 to 10 hours. Step (ii) of the process of the present invention should be carried out under lower temperature conditions, e.g. −20 to 30° C. over a period of 0.5 to 24 hours due to the low boiling point of acetaldehyde. The addition should be controlled to minimise self-condensation of the acetaldehyde. Preferably the reaction is performed at −20 to 25° C. over a period of 3 to 10 hours.

The Lewis acidic metal salt, terminal alkyne, cyclic amine base, alkanolamine ligand and acetaldehyde molar ratios can be varied substantially, leading to an increase in the yields and enantioselectivities. The terminal alkyne may be preferably present in large molar excess (e.g. >10 moles per mole of acetaldehyde) and acts as the reaction medium for step (i) of the process. Otherwise the acetaldehyde and terminal alkyne (in the form of the metal-alkyne complex) may be combined in the range 1.3:1 to 1:1.3 moles (alkyne:acetaldehyde). The Lewis acidic metal salt may be added at a molar ratio in the range 0.05:1 to 3:1, preferably 1:1 to 2:1, particularly 1.5:1 (Lewis acidic metal salt:acetaldehyde). The cyclic amine base may be added at a molar ratio in the range of 0.3:1 to 3:1, preferably 1:1 to 2:1, especially 1.6:1 (cyclic amine base: acetaldehyde). The alkanolamine ligand may be added at a molar ratio in the range 0.05:1 to 3:1, preferably 1:1 to 2:1, particularly 1.6:1 (alkanolamine ligand:acetaldehyde).

The reaction product of the process of the present invention may be recovered from the reaction mixture using work-up procedures known to those skilled in the art. For example, the reaction may be quenched by addition of saturated aqueous ammonium chloride ($NH_4Cl$) solution and the resulting aqueous layer extracted with an ether. The ether may be washed with saturated aqueous sodium chloride (NaCl) solution and dried (e.g. over anhydrous magnesium sulphate ($MgSO_4$)), filtered and concentrated in vacuo. Yield and enantioselectivity may be determined using standard analytical methods, e.g. gaschromatographic (GC) analysis.

In one preferred embodiment, we have found that the combination of slow addition of acetaldehyde to the metal-alkyne complex in excess alkyne, wherein the metal-alkyne complex is formed in the presence of DBU and (+) N-methylephedrine affords an acetaldehyde-derived hydroxyalkyne product in considerably improved yields.

The acetaldehyde-derived hydroxyalkyne product of step (ii) may if desired be subjected to a thermal fragmentation reaction (iii) to remove the group attached to the alkyne to provide a hydroxyalkyne product for example using 2-methyl-3-butyn-2-ol (I) as follows;

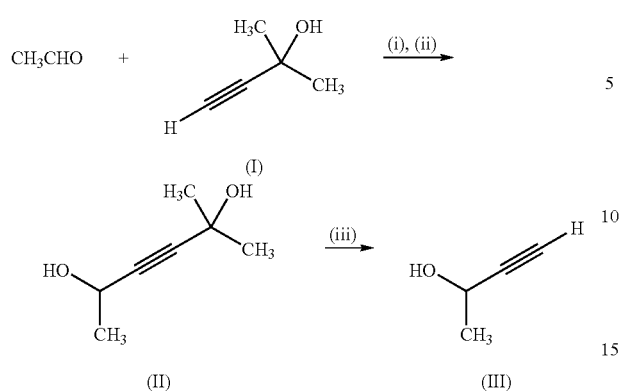

The thermal fragmentation reaction (iii) may be performed using the methods described in Carreira et al, *Organic Letters*, 2000, 2(26), 4233-4236, and generally involves heating the hydroxyalkyne product in the presence of an inorganic base, e.g. potassium carbonate and optionally a crown ether, e.g 18-C-6. A preferred product of step (iii) is 2-hydroxybut-3-yne (III). The resulting thermally fragmented hydroxyalkyne is consequently itself a terminal alkyne and may, if desired, be further reacted with a second aldehyde molecule and hydrogenated according to the process of WO 02/094741 to yield an unsymmetrical 1,4-diol or may be reacted with a further equivalent of acetaldehyde according to the method of the present invention to yield hexyne-2,5-diol, [$CH_3C(OH)C \equiv CC(OH)CH_3$]. If desired the hexyne-2,5-diol may be hydrogenated using methods know in the art to hexene-2,5-diol or hexane-2,5-diol.

Where the product of the process is, or is used to prepare a thermally stable diol, the diols may be used in the synthesis of a range of cyclic phosphines using methods known to those skilled in the art. If chiral diols are chosen, the resulting chiral cyclic phosphines may be used for the construction of asymmetric catalysts useful for example, for asymmetric hydrogenation (see for example Burk et al, *J. Am. Chem. Soc.*, 1995, 117, 4423-4424, Scheme 1)

EXAMPLES

The invention is further illustrated by reference to the following examples.

All reactions were performed using oven-dried glassware under an atmosphere of dry nitrogen. Toluene was distilled and dried before use. Reagents were purchased from Fluka or Aldrich chemical companies, and used without further purification except acetaldehyde, which was distilled before use.

Example 1

Comparative Example

Using a general procedure for the nucleophilic addition of terminal alkynes to aldehydes in solvent as proposed by Frantz, D. E.; Fässler, R.; Carreira, E. M. *J. A. Chem. Soc.* 2000, 122, 1806-1807. Example 1.1: A 10 mL flask was charged with zinc triflate (200 mg, 0.550 mmol, 1.1 eq) and (+)-N-methylephedrine (108 mg, 0.602 mmol, 1.2 eq) and purged with nitrogen for 15 min. To the flask was added toluene (1.5 mL) and triethylamine (61 mg, 0.602 mmol, 1.2 eq). The resulting mixture was stirred at 23° C. for 2 hours before the alkyne, 2-methyl-3-butyn-2-ol (I) (0.600 mmol, 1.2 eq) was added by syringe in one portion. After 15 min of stirring acetaldehyde (0.5 mmol, 1.0 eq) was added in one portion by syringe. The reaction was allowed to stir overnight and then quenched by the addition of saturated aqueous ammonium chloride ($NH_4Cl$) solution (3 mL). The reaction mixture was poured into a separating funnel containing diethyl ether (10 mL). The layers were separated and the aqueous layer was extracted with diethyl ether (3×10 mL). The combined organic layers were washed with brine (10 mL), dried over anhydrous $MgSO_4$ and concentrated in vacuum.

The products were analysed using gas chromatography (GC). GC method: Lipodex-E column, 95° C., 55 psi, retention time: 16.6 min (minor isomer), 17.5 min (major isomer).

The above experiment was repeated (Examples 1.2-1.8), changing solvent for step (i), amine base and reaction temperature.

The conditions and results for Examples 1.1-1.9 are depicted in the following Table.

| Example | Solvent | $Zn(OTf)_2$ eq[2] | Base | Base eq[2] | Alkanolamine ligand | Ligand eq[2] | Temp. | Yield % | ee[4] % |
|---|---|---|---|---|---|---|---|---|---|
| 1.1 | Toluene | 1.1 | $Et_3N$ | 1.2 | nme[3] | 1.2 | 23 | <20 | 60 |
| 1.2 | Toluene | 1.1 | $Et_3N$ | 1.2 | nme | 1.2 | 30 | 0 | — |
| 1.3 | Toluene | 1.1 | $Et_3N$ | 1.2 | nme | 1.2 | 40 | 0 | — |
| 1.4 | $CH_2Cl_2$ | 1.1 | $Et_3N$ | 1.2 | nme | 1.2 | 20 | 0 | — |
| 1.5 | Toluene | 1.1 | $IPr_2EtN$ | 1.2 | nme | 1.2 | 20 | <20 | 50 |
| 1.6 | Toluene | 1.1 | pyridine | 1.2 | nme | 1.2 | 20 | 0 | — |
| 1.7 | Toluene | 1.1 | DBU | 1.2 | nme | 1.2 | 20 | <20 | 60 |
| 1.8 | Toluene[1] | 1.1 | DBU | 1.2 | nme | 1.2 | 20 | 0 | — |
| 1.9 | iPrOH | 1.5 | DBU | 1.6 | nme | 1.6 | 20 | 0 | — |

[1]Solvent increased by a factor of 20 (volume).
[2]eq = equivalents, i.e. moles per mole acetaldehyde
[3]nme = (+)-N-methylephedrine.
[4]ee % = enantiomeric excess In all cases the yield of (R)-2-methylhex-3-yne-2,5-diol (II) was always less than 20% (based on acetaldehyde). Changing the solvent, base and relative amounts of zinc triflate, base and alkanolamine ligand did not increase the yield.

Example 2

Reaction of acetaldehyde with 2-methyl-3-butyn-2-ol

Step (i): Zinc triflate (10.9 g, 30 mmol, 1.5 eq), (+)-N-methylephedrine (5.7 g, 32 mmol, 1.6 eq), DBU (4.8 mL, 32 mmol, 1.6 eq) and 2-hydroxy-2-methyl-3-butyne (Alkyne 1, 80 mL) were stirred at room temperature for 2 h. Step (ii): a solution of acetaldehyde (1.13 mL, 20 mmol) in toluene (50 mL) was then slowly added over a 4 hour period. After stirring overnight at room temperature, the reaction was quenched by addition of sat. aq. $NH_4Cl$ (50 mL). The combined organic layers were washed with sat. aq. NaCl (100 mL), dried ($MgSo_4$), filtered and concentrated in vacuo. Purification of the crude material by filtration through a plug of silica afford 2.25 g of (II) as a yellow oil in 87% yield and 67% ee as determined by GC analysis. GC method; Lipodex-E column, 95° C., 55 psi, retention time: 16.6 min (minor isomer), 17.5 min (major isomer).

The above experiment was repeated whereby the second step (ii) was carried out at 0° C. or −10° C. The yields were 50% or greater and the enantioselectivities were also 67%.

This example demonstrates the surprising effect that by omitting the solvent for metal-alkyne complex formation the process of the present invention provides acetaldehyde-derived hydroxyalkynes in high yield.

Example 3

Thermal Fragmentation of (II) to Yield 2-hydroxybut-3-yne

The isolated reaction product from Example 2, (R)-2-Methylhex-3-yne-2,5-diol, was mixed with 1.5 equivalents of $K_2CO_3$ in toluene. The reaction flask was then placed in the Kugelrohr oven and heated at 120° C. under vacuum. As the thermal fragmentation reaction takes place, (R)-(+)-3-butyn-2-ol was gradually distilled off the reaction mixture and collected in 40-60% yield.

The invention claimed is:

1. A process for performing a coupling reaction between acetaldehyde and a terminal alkyne to yield a hydroxyalkyne comprising the steps of;
   (i) reacting without solvent, a terminal alkyne with zinc triflate in the presence of (+) -or (−)-N-methylephedrine and a cyclic amine base selected from the group consisting of 1,8-diazabicyclo[5.4.0]undec-7-ene (DBU), 1,5-diazabicyclo-[4.3.0]non-5-ene and 1,4-diazabicyclo [2.2.2]octane, to form a metal-alkyne complex, and
   (ii) adding a solution of acetaldeyde in a solvent selected from the group consisting of a hydrocarbon, an aromatic hydrocarbon, an ether, an alcohol and a chlorinated hydrocarbon to the metal alkyne complex.

2. A process according to claim 1 wherein the terminal alkyne is of general formula $R^1R^2C(OH)C\equiv CH$ in which $R^1$ and $R^2$ may be the same or different and are selected from the group consisting of methyl, ethyl and propyl.

3. A process according to claim 1, wherein the acetaldehyde concentration is between 0.1 and 2 moles/liter.

4. A process according to claim 1, wherein step (ii) is performed at −20 to 25° C. over a period of 3 to 10 hours.

5. A process according to claim 1, wherein the molar ratio of zinc triflate:acetaldehyde is 1.5:1, the molar ratio of cyclic amine base:acetaldehyde is 1.6:1 and the molar ratio of (+)- or (−)-N-methylephedrine to acetaldehyde is 1.6:1.

6. A process according to claim 1, wherein the molar ratio of zinc triflate:acetaldehyde is in a range of 0.05:1 to 3:1, the molar ratio of cyclic amine base:acetaldehyde is in a range of 0.3:1 to 3:1, and the molar ratio of (+)- or (−)-N-methylephedrine to acetaldehyde is in a range of 0.05:1 to 3:1.

7. A process according to claim 1, wherein the molar ratio of zinc triflate:acetaldehyde is in a range of 1:1 to 2:1, the molar ratio of cyclic amine base:acetaldehyde is in a range of 1:1 to 2:1, and the molar ratio of (+)- or (−)-N-methylephedrine to acetaldehyde is in a range of 1:1 to 2:1.

* * * * *